(12) United States Patent
Hong et al.

(10) Patent No.: US 6,589,572 B2
(45) Date of Patent: Jul. 8, 2003

(54) **HYPERTENSION-TREATMENT AND CHOLESTEROL-DEPRESSANT COMPOSITION COMPRISING EXTRACT FROM MIXTURE OF *PANAX NOTOGINSENG* AND *SALVIA MILTIORRHIZA* AND METHOD OF PREPARING THE SAME**

(75) Inventors: Eun Kyung Hong, Seoul (KR); Young Shin Chung, Seoul (KR)

(73) Assignee: Medvill Co., Ltd., Seoul (KR)

( * ) Notice: Subject to any disclaimer, the term of this patent is extended or adjusted under 35 U.S.C. 154(b) by 0 days.

(21) Appl. No.: 09/880,274

(22) Filed: Jun. 14, 2001

(65) Prior Publication Data
US 2003/0003165 A1 Jan. 2, 2003

(51) Int. Cl.[7] .......................... A01N 35/78; A61K 9/48; A61K 9/66; A61K 9/20
(52) U.S. Cl. ...................... 424/728; 424/746; 424/451; 424/455; 424/464
(58) Field of Search ................. 424/725, 728, 424/746, 451, 455, 464; 514/2, 824

(56) References Cited

U.S. PATENT DOCUMENTS 5,358,962 A  * 10/1994 Oura et al.

FOREIGN PATENT DOCUMENTS

| CN | 1100657  | * | 3/1995  |
| CN | 1112424  | * | 11/1995 |
| CN | 1219400  | * | 6/1999  |
| JP | 04141064 | * | 5/1992  |
| JP | 04159220 | * | 6/1992  |
| JP | 07238027 | * | 9/1995  |
| JP | 63267798 | * | 3/1996  |

OTHER PUBLICATIONS

Lei et al., Am J Chinese Medicine (1986), 14(3–4): 145–152. Cardiovascular pharmacology of *Panax notoginseng* (Burk) F.H. and *Salvia miltiorrhiza*.*
Leung et al., Neurochem Res (1991), 16(6): 687–692. Reduction of cellular damage induced by cerebral ischemia in rats.*
Ogawa et al., J Japanese Society of Nutrition and Food Sciences (1997), 50(2): 127–132. Effect of Tienchi ginseng powder on blood pressure and lipid metabolism in SHRSP (stroke–prone spontaneously hypertensive rats).*
Xu et al., China J Chinese Materia Medica (1993), 18(6): 367–369. Studies on blood–lipid decreasing action of total saponins of *Panax notoginseng* (Burk.) F.H. Chen.*

* cited by examiner

Primary Examiner—Christopher R. Tate
Assistant Examiner—Michele C. Flood
(74) Attorney, Agent, or Firm—Lowe Hauptman Gilman & Berner, LLP

(57) ABSTRACT

A composition for treating hypertension and lowering cholesterol is provided which contains the mixed extract of *Panax notoginseng* and *Salvia miltiorrhiza* as an active ingredient thus lowering and maintaining blood pressure substantially constant. Also provided is a method for preparing composition containing the mixed extract of *Panax notoginseng* and *Salvia miltiorrhiza* as an active ingredient.

6 Claims, 16 Drawing Sheets

HYPERTENSION-TREATMENT AND CHOLESTEROL-DEPRESSANT COMPOSITION COMPRISING EXTRACT FROM MIXTURE OF *PANAX NOTOGINSENG* AND *SALVIA MILTIORRHIZA* AND METHOD OF PREPARING THE SAME

TECHNICAL FIELD

The present invention relates to a composition for treating hypertension and lowering cholesterol and a method for preparing same. More specifically, the present invention relates to a composition for treating hypertension and lowering cholesterol which contains the mixed extract of *Pana notoginseng* and *Salvia miltiorrhiza* as an active ingredient, and a method for preparing same.

BACKGROUND ART

Cardiac and vascular diseases are one of the main causes of human death, and are represented by cerebral hemorrhage, cerebral thrombosis, heart failure, cardiac infarction, etc. However, etiology of such diseases is very diverse and complex. The target for treatment of hypertension is to prevent the occurrence of complications in brain, heart, kidney, liver, etc., thereby allowing the human to manage a normal life by the average life span. The development of drugs for treatment of hypertension is still urgently required.

Blood pressure and hypertension will be more specifically explained hereinbelow. The term, blood pressure, denotes a pressure of blood stream flowing through blood vessels, i.e., arterial pressure. In this context, the term, hypertension, means that a certain cause induces an increase of resistance on the internal wall of blood vessel thus resulting in the maximum blood pressure (systolic blood pressure or highest blood pressure) of 150–160 mmHg and the minimum blood pressure (diastolic blood pressure or lowest blood pressure) of 90 mmHg or more. The former is called a systolic hypertension and the latter is called a diastolic hypertension. Although both may separately arise, it is general that they are simultaneously present. Moreover, hypertension may occur in the thirties, but it mainly occurs during the pre- and post-climacteric period in men rather than women.

According to etiology, hypertension can be classified into essential hypertension and symptomatic hypertension. Although the cause of essential hypertension is not fully clarified as yet, essential hypertension occurs in many cases of fatty persons having a potent genetic predisposition. However, essential hypertension may also be observed in many cases of otherwise persons This essential hypertension is closely related to arteriosclerosis. In this context, it appears that hypertension may result in arteriosclerosis rather than arteriosclerosis which is the cause of hypertension. In case of essential hypertension, blood pressure is fluctuated at the early stage and then is maintained at a high level when artery is hardened.

Symptomatic hypertension arises from other cause and is mainly induced by renal diseases, particularly acute nephritis, toxemia of pregnancy, climacteric disorders, etc.

In many cases, hypertension at the early stage does not develop any symptom and is accidentally revealed through measurement of blood pressure. When hypertension is progressed, various subjective symptoms such as headache, anxiety, fatigue, vertigo, palpitation, excitation and constipation are developed and blood pressure is greatly fluctuated. In a chronic state of disease, hypertrophic extension of left ventricle, coronary artery disorders, heart failure, etc. are progressed to either cause congestive heart failure or cardiac infarction, which may lead to death, or to cause change in a renal artery and resultant nephrosclerosis which may be a culprit of renal failure such as polyuria, night polyuria, proteinuria, etc., the patient of which may lead to death because of uremia. Other complications such as arteriosclerosis on eyeground, aneurysm etc., may also be developed.

Although the cause of hypertension is very diverse, hypertension stems generally from hyperergasia of sympathetic nerve, abnormality of hormone secretion, abnormality of renal artery, etc. Thus, spontaneous hypertension is concerned with at least three or more genes, upon which environmental factors such as excess ingestion of salts or stress act to induce hypertension. In the early stage of disease, the neurological factors play an important role and the disease is progressed by factors including abnormalities of metabolism and structure of blood vessels. If hypertension is persisted, the contraction of artery is fixed, plasma norepinephrine is reduced, and collagen and non-collagen metabolism in cardiovascular system is accelerated, thereby fixing the state of hypertension. A change in the lining of blood vessel to support the elevated pressure thereof affects the blood flow toward heart and kidney thus increasing the mortality due to diseases in circulatory system such as arteriosclerosis, cardiac infarction, cerebral stroke, etc.

The study of hypertension has been actively and continuously conducted with a medical concern in an effort to induce development of several therapeutic agents from about 40 years ago. However, the prior therapeutic agents have many problems due to continuous medication and therefore, a satisfactory therapeutic agent for hypertension has not been developed as yet. It has been reported that hypertension can be preferably treated by means of a combination of two or three different kinds of hypotensive agents. By way of example, it is preferred that a drug having hypotensive effect is used, while another drug having different hypotensive mechanism is administered, to reduce any possible side effect of the drug as first used.

Side effects, which may be caused by currently used hypotensive agents are as follows:

Diuretic-based antihypertensive agents have a tendency to induce hypocalcemia, hyperuricemia, glycosemia, hyperlipidemia, sexual function disturbance, hyperkalemia, etc., whereas sympatholytic hypotensive agents may induce sexual function disturbance, thirst, depression, orthostatic hypotension, bradycardia, asthma, heart failure, etc.

Vasodilating hypotensive agents show tachycardia, arrhythmia, asthenia, polyuria, suffusion, headache, bradycardia, etc.

In addition, angiotensin II inhibitors show side effects such as rapid decrease in renal function, uremia, heart failure, etc., and agents for blocking 5-HT receptor may induce headache, dry mouth, nausea, vertigo, eruption, pruritus, cacogeusia, pyrexia, leukocytopenia, kidney failure, arthralgia, etc.

The effectiveness of recently developed $Ca^+$ antagonists has been substantially established. It has been revealed, however, that they have side effects such as inhibition of cardiac function due to myocardial contraction, and further that $Ca^{2+}$ participates in insulin secretion mechanism to induce disorder of insulin secretion.

Thus, the use of many therapeutic agents for hypertension accompanies a serious practical problem due to such side effects. In addition, in controlling the blood pressure, if any one side is inhibited, the other side may be accelerated to induce a new unbalance of hypertension. By way of example, the administration of diuretic-based hypotensive agent may lower water or sodium factors and on the other hand, accelerate rennin-angiotensin system.

The blood pressure is maintained in a competitive manner by factors conflicting with each other. However, the effect following administration of hypotensive agents is substantially unsatisfactory to treat hypertension and, if any resistance to the drug is raised, an antagonistic factor at any one side may be accelerated. Therefore, when two or more hypotensive agents are used together, it is preferred that the mechanism thereof be different from each other. Preferred agents for treatment of hypertension should improve blood flow in tissues and organs by preventing any possible disorder of the target organ and controlling blood pressure, maintain blood pressure within the normal range, and have substantially no toxicity and side effect.

Meanwhile, *Panax notoginseng* NEES, which is one of medicinal herbs, is a perennial herbal plant belonging to Araliaceae and contains approximately 4% of saponin aglycons (Ginsenosides Ro, a, b1, b2, c, d, e, f, g1, g2, h). Aglycon of ginsenoside Ro is oleanolic acid; aglycon of ginsenosides Rb1, b2, c and d is 20-s-protopanaxadiol; and aglycon of ginsenosides Re, g1 and g2 is 20-s-protopanaxtriol. In addition, *Panax notoginseng* also contains, β-sitosterol, β-sitosteryl-glucoside,panaxynol (1,9-cis)-heptadecadiene-4,6-dyen-3-ol), vitamin B group, choline, etc., and further, about 1.5% of monosaccharides, and disaccharides, trisaccharides, etc. None of components contained in *Panax notoginseng* has been known to have pharmacological activities, except that it has been reported that aglycons have hypotensive activity in animals.

Since *Panax notoginseng* tends to exhibit hemostatic activity, it has been used for hematemesis or rhinorrhagia, and further stimulates the function of brain by acting on central nervous system. In addition, it has been known that *Panax notoginseng* exhibits hypotensive activity, dilation of heartbeat and increase in coronary blood flow, while showing lipidolysis activity in blood and activating immune function.

Another medicinal herb, *Salvia miltiorrhiza* BUNGE belonging to Labiatae is a perennial herbal plant spontaneously growing in fields and mountains on the northeast area of China. It has been known that *Salvia miltiorrhiza* BUNGE contains phenanthraquinone-based pigment including tanshinone I purplish brown (I), tanshinine II red (II), cryptotanshinone orange (III), and other tanshinol I, II. However, it has not been disclosed as yet that any of these components exhibits pharmacological activities. Merely known is that the aqueous extract of *Salvia miltiorrhiza* BUNGE has some inhibitory activity against various dermatomycosis. In the filed of Chinese medicine, it has been used for treating dysmenorrhea, menorrhalgia, menopause or postpartal abdominal pain. In this context, it is supposed that phenanthraquinone-based pigment materials are highly possible to take part in endocrine system in view of their chemical structures and are also concerned with disturbance of blood circulation.

DISCLOSURE OF THE INVENTION

In consideration of the problems inherent in the prior art, it is an object of the present invention to provide a medicinal herb composition for treating hypertension and lowering cholesterol level.

Another object of the invention is to provide a composition for treating hypertension and lowering cholesterol level, in which the plant extract exhibits a significant hypotensive effect with substantially no side effect and regulates the factors responsible for the control of blood pressure to adjust blood pressure within normal range, thereby maintaining the homeostasis of blood pressure, and further to provide a method for preparing same.

BRIEF DESCRIPTION OF DRAWINGS

For better understanding of the nature and purposes of the present invention, reference should be made to the following detailed description taken in connection with the accompanying drawings, in which.

BEST MODE FOR CARRYING OUT THE INVENTION

Figure 1:
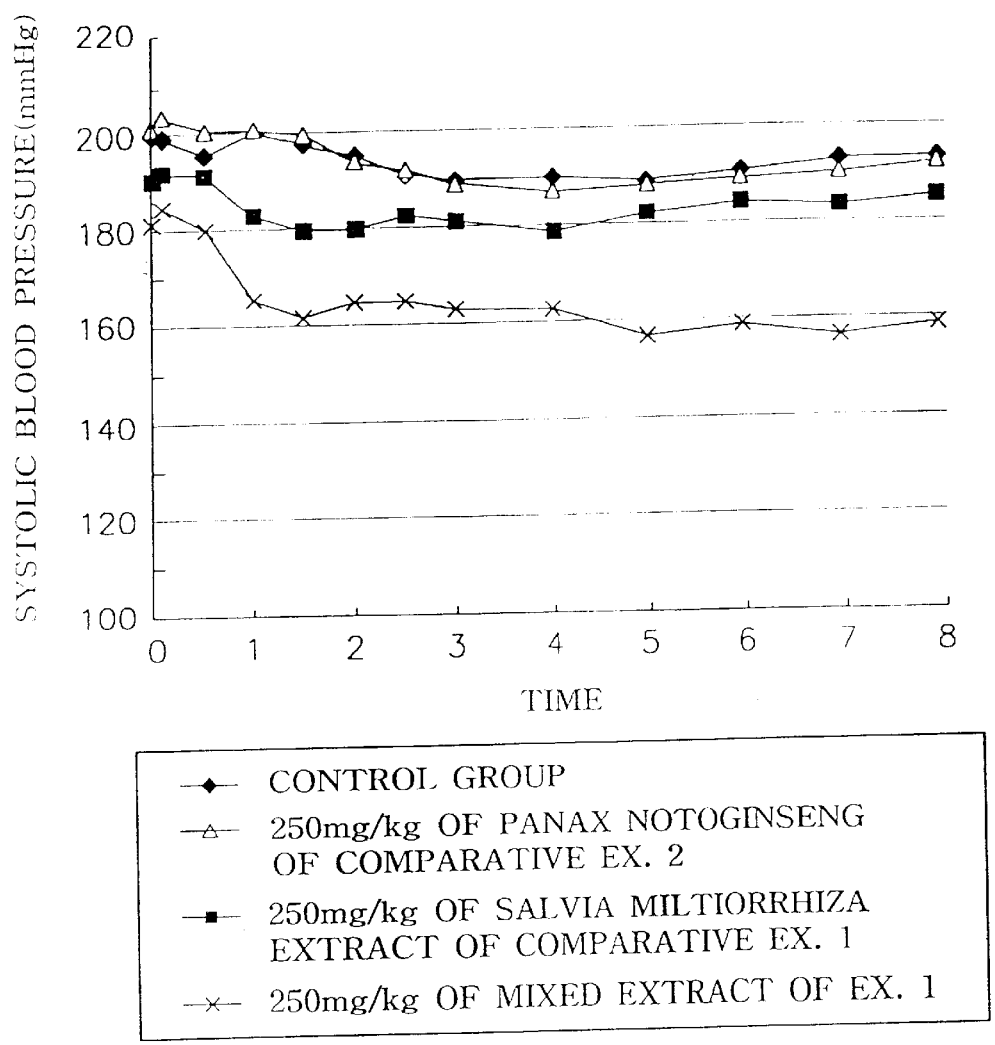
FIG. 1 is a graph showing the effects of lowering systolic blood pressure following a single oral administration of the extract of each of *Panax notoginseng* and *Salvia miltiorrhiza* and the mixed extract of *Panax notoginseng* and *Salvia miltiorrhiza* in comparison with each other, as a result of Comparative Example 3, Comparative Example 4 and Example 8.

The present inventors have found that the combined use of two kinds of medicinal herbs, i.e. *Panax notoginseng* and *Salvia miltiorrhiza* has far greater effect of lowering blood pressure than the independent use of the respective herbal plants and have completed the present invention.

To achieve the above-mentioned purposes of the present invention, a composition for treating hypertension and lowering cholesterol level, which contains the mixed extract of *Panax notoginseng* and *Salvia miltiorrhiza* as an active ingredient is provided.

The composition of the present invention can be formulated into the composition selected from the group consisting of tablets, capsules, solutions, suspensions, syrups and edible beverages, by further incorporating a pharmaceutically acceptable excipient.

It is preferred that the mixed medicinal herb extract of the present invention is an aqueous extract or an alcoholic extract.

In the mixture of *Panax notoginseng* and *Salvia miltiorrhiza*, the mixing ratio thereof is preferably 5:1 to 1:5, and more preferably 2:1 to 1:2, on the basis of weight. If the mixing ratio is beyond the above-specified range, the synergistic effect derived from the mixed extract is low.

The dosage of the mixed extract of *Panax notoginseng* and *Salvia miltiorrhiza* is preferably 10 to 40 mg per 1 kg of the body weight of an adult man.

In addition, the present invention provides a method for preparing the composition for treating hypertension and lowering cholesterol level, which comprises the steps of:

a) mixing *Panax notoginseng* and *Salvia miltiorrhiza* and extracting the mixture with water;
b) filtering the extract obtained in the above step a);
c) saturating the filtrate obtained in the above step b) at a temperature of 100 to 140° C. and under an elevated pressure to produce protein precipitate, which is then removed by centrifuge;
d) extracting the precipitate-removed filtrate of the above step c) with an organic solvent and separating the aqueous layer with removing the oil-soluble materials from the filtrate; and
e) lyophilizing the aqueous layer separated in the above step d).

The method of the present invention further includes the step of preparing the formulation selected from the group consisting of tablets, capsules, solutions, suspensions, syrups and edible beverage by incorporating a pharmaceutically acceptable excipient into the lyophilized mixed extract of *Panax notoginseng* and *Salvia miltiorrhiza* as obtained from the above step e).

The amount of water used for extraction in the above step a) is preferably 5 to 10 times, particularly 7 times, greater than the weight of the mixture of *Panax notoginseng* and *Salvia miltiorrhiza*.

The organic solvent used in the above step d) is preferably chloroform or hexane.

Alternatively, the present invention also provides a method for preparing the composition for treating hypertension and lowering cholesterol level, which comprises the steps of:

a) extracting the mixture of *Panax notoginseng* and *Salvia miltiorrhiza* with one or two kinds of alcohols for 48 to 72 hours at room temperature while stirring;
b) filtering the extract obtained in the above step a) to separate the extract into the residue and the filtrate; and
c) removing alcohol from the filtrate obtained in the above step b) to obtain the extract in the form of powder.

The alcohol used in the above step a) is preferably 70 to 80% alcohol, particularly alcohols having 1 to 5 carbon atoms such as methanol, ethanol, propanol, butanol and pentanol.

The method of the present invention further includes the step of preparing the formulation selected from the group consisting of tablets, capsules, solutions, suspensions, syrups and edible beverage by incorporating a pharmaceutically acceptable excipient into the alcoholic extract of *Panax notoginseng* and *Salvia miltiorrhiza* as obtained from the above step c).

The present invention provides a novel pharmaceutical composition containing the extract of the mixture composed of medicinal herbal plants including *Panax notoginseng* and *Salvia miltiorrhiza*. The extract has no pathological or physiological influence upon normal tissues and functions thereof, and has an effect of activating the function to maintain the homeostasis of blood pressure by participating in the mechanism of controlling blood pressure. However, the use of only one of *Panax notoginseng* and *Salvia miltiorrhiza* provides no expectable hypotensive effect.

The hypotensive effect of the composition according to the present invention could be confirmed by experiments using animals suffering from genetically induced hypertension, namely, spontaneously hypertensive rats (SHR). Currently used antihypertensive agents control hypertension in the manner of symptomatic treatment whereas the composition of the present invention lowers blood pressure by exhibiting CNS inhibitory activity and a potent sedative effect, and at the same time, secondarily inhibiting sympathetic nerve to interfere the entrance of hypertensive substances such as noreinephrine, serotonin and hypertensin into the reservoir. Further, the composition of the present invention also induces the expression of antagonistic substances against hypertensive hormones released from posterior lobe of hypophysis, decreases the resistance of peripheral blood vessel and exhibits activities of increasing new blood flow and relaxing the tension of cerebral blood vessel.

Therefore, the composition of the present invention is characterized in that it provides a superior hypotensive effect but does not decrease the blood pressure to below the normal range, and further that it has no influence upon normal blood pressure and hypotension. In addition, the composition of the present invention does not show any detectable side effect in the course of controlling hypertension but exhibits a progressive and continuous effect of treating hypertension.

In other words, the composition of the present invention, a drug for improving a disorder of blood circulation, has a cardiotonic activity, increases blood flow in coronary artery and reduces oxygen consumption, while at the same time, exhibiting a potent sedative activity.

The composition showing the above-mentioned effects has been developed by the inventors of the present invention through a prolonged experimental study using numerous medicinal herbs related to the controlling of blood pressure, from which it has been confirmed that the novel composition comprising *Panax notoginseng* and *Salvia miltiorrhiza* extract exhibits a superior hypotensive activity and has substantially no toxicity and side effects. As a result, we have completed the present invention.

In view of the fact that the pharmacologically active components contained in those herbal plants has an effect of improving abnormal symptoms occurring in cardiac system and blood circulation, we have applied the composition of the present invention to hypertension and observed that the composition of the present invention has no side effect on cardiac system and cerebrovascular system and exhibits an effect of smoothly controlling and improving blood pressure. Further, the inventive composition serves to keep the blood pressure above the normal value, thus preventing any abnormal symptom.

The main components of the composition according to the present invention are saponin and aglycons thereof. However, it has not been identified as yet that the hypotensive effect of the composition of the present invention is induced by these main components. Recently, in China it has been reported that ginseng plants increase the blood flow in coronary artery of animals and exhibit an effect of reducing oxygen consumption by cardiac muscle to reduce the load of heart. In addition, the extract of the present invention is concerned with the endocrine system, and particularly, improves the disorder of blood circulation due to clotting factor. The composition of the present invention makes the function of blood circulatory and cardiovascular systems smooth and can be continuously used with little side effect.

In the composition of the present invention, the mixed extract of *Panax notoginseng* and *Salvia miltiorrhiza* is used after removing resins, proteins and fibroid materials therefrom. In case of the aqueous extract, *Panax notoginseng* and *Salvia miltiorrhiza* are first macerated or digested in tap water or distilled water and then filtered, and chloroform or hexane is added to the filtrate to remove resins, proteins and fibroid materials. Then, the mixed extract of *Panax notoginseng* and *Salvia miltiorrhiza* is purified with addition of talc and then pulverized by lyophilization.

When the mixed extract of *Panax notoginseng* and *Salvia miltiorrhiza* as obtained according to the present invention is administered to hypertensive rats, a significant hypotensive effect was observed as the amount thereof increases.

Hereinafter, the method for preparing the mixed extract according to the present invention is more specifically explained.

According to the method for extracting the aqueous extract of the present invention, in the first step dried *Panax notoginseng* and *Salvia miltiorrhiza* are mixed, ground and then extracted by means of water such as tap water or distilled water as the solvent with heating or heating under saturated vapor pressure (100–140° C.). The amount of water used for extracting the mixture of *Panax notoginseng* and *Salvia miltiorrhiza* is 5 to 7 times, particularly preferably 7 times, as much as the dried material.

Then, in the second step, the extract is centrifuged to remove the precipitate and again boiled under saturated vapor pressure (100–140° C.) to coagulate the remaining proteins, which is then filtered by centrifuge and removed.

In the third step, the separated filtrate is extracted with an organic solvent such as chloroform, hexane, dichloromethane, cyclohexane, etc., preferably chloroform or hexane, to remove the impurities including resins and fibroid materials, and the aqueous layer is again purified with talc and then lyophilized to obtain the desired aqueous mixed extract.

The alcoholic extract obtained by using an alcohol as the solvent for extraction of the mixture of *Panax notoginseng* and *Salvia miltiorrhiza*, which is an alternative method according to the present invention, can provide the same effect of the aqueous extract as defined above. The specific method for obtaining the alcoholic extract is as follows.

The medicinal herbs, *Panax notoginseng* and *Salvia miltiorrhiza*, are independently ground, and then mixed together in the ratio of 5:1 to 1:5, preferably in the ratio of 2:1 to 1:2, by weight. The mixture is eluted with one or two kinds of alcohols, preferably 70 to 80% alcohols, at the room temperature for 48 to 72 hours while concomitantly stirring. The eluate is decanted off, and the residue is re-extracted with alcohol having the same concentration according to the same manner as above and the eluate is decanted off and then combined with the first eluate. Talc is added to the eluate, which is remained after recovering alcohol, stirred and then centrifuged. The supernatant is decanted off and then filtered. The filtrate is pulverized after removing alcohols.

The mixed extract (aqueous extract and alcoholic extract) of *Panax notoginseng* and *Salvia miltiorrhiza* as obtained according to the above-mentioned methods of the present invention can be effectively used as the pharmacologically valuable composition for lowering blood pressure as described above.

The present inventors have confirmed that the composition of the present invention exhibits a good hypotensive activity and further, demonstrated that the composition of the present invention is a safe drug which has passed through acute toxicity test.

In using the mixed extract of *Panax notoginseng* and *Salvia miltiorrhiza* according to the present invention for the clinical purpose, the therapeutically effective amount of the mixed extract can be formulated alone or in combination with a pharmaceutically acceptable carrier into a suitable pharmaceutical preparation according to the conventional method used in the pharmaceutical field, and then, administered according to a conventional manner used in the pharmaceutical field, preferably via oral route. In general, the composition of the present invention can be formulated into the oral dosage form, for example, tablets, capsules, solutions, suspensions or syrups or can be prepared in the form of a beverage.

Although the dosage of the mixed extract of the present invention may vary depending on the severity of diseases to be treated, the sex, age and weight of a patient, the kind of the desired effect, etc., the oral daily dosage for an adult man is generally 5–50 mg, preferably 10–40 mg, per 1 kg of the body weight.

The present invention is more specifically explained by the following examples and comparative examples. However, it should be understood that these examples are provided only for illustration of the present invention but not intended to limit the present invention in any manner.

EXAMPLES

Example 1

Preparation of the Aqueous Mixed Extract of *Panax notoginseng* and *Salvia miltiorrhiza*

Dry *Panax notoginseng* and *Salvia miltiorrhiza* were respectively ground and then mixed in the ratio of 5:4 by weight. 90 g of the mixture was taken and 3000 ml of distilled water or tap water was added thereto. The mixture was then extracted for 40–60 minutes at temperature of 121° C. under saturated vapor pressure of 15 psil in an autoclave, and the extract was separated with removing the residue.

The extract was centrifuged to remove the precipitate and then the aqueous filtrate was filtered, concentrated with distillating to reduce its total volume to 1500 ml and then filtered. The filtrate was saturated again for 15 minutes at temperature of 121° C. under saturated vapor pressure of 15 psi in an autoclave to produce the precipitate containing coagulated proteins, centrifuged to remove the precipitate and then filtered.

The filtrate was introduced into a separatory funnel. 400 ml of chloroform was added thereto to extract resins and fibroid materials and then the chloroform layer was separated and removed. The same procedure was repeatedly practiced two times. Then, 200 ml of n-hexane was added to the aqueous layer to extract the remaining proteins, resins, fibroid materials and n-hexane-soluble materials.

The aqueous layer was separated, warmed to 60–80° C., stirred with 500 g of talc and then filtered under reduced pressure to remove talc. The filtrate was slowly filtered again, and the filtrate was pulverized by lyophilization.

According to the above method, a total of 15 g (corresponding to the yield of about 17% based on the dry weight) of the desired mixed aqueous extract was obtained from the mixed extract of *Panax notoginseng* and *Salvia miltiorrhiza*.

Example 2
Preparation of the Alcoholic Mixed Extract of *Panax notoginseng* and *Salvia miltiorrhiza*

100 g of dry *Panax notoginseng* radix and 100 g of dry *Salvia miltiorrhiza* were separately ground and mixed together in the ratio of 5:4 by weight. To the mixture was added 1.2 ι of 70% ethanol. The mixture was extracted for 48–72 hours with concomitantly stirring. The extract was decanted off, and the remaining residue was re-extracted with addition of a given amount of 70% ethanol according to the same manner as above.

The re-extract was decanted off and combined with the first extract. Alcohol was recovered from the combined extract by means of a refluxing condenser, and then the remaining extract was mixed with talc, stirred and centrifuged to remove the precipitate. The remaining supernatant was filtered.

Then, n-hexane and chloroform were added to the filtrate to remove resins, proteins and fibroid materials, and the remaining solution was then pulverized by lyophilization. According to this method, the brown powder was obtained in the yield of 20%.

Example 3
Preparation of Tablets 250 mg of the lyophilized powdery mixed extract as obtained in Example 1 was blended with 260 mg of lactose for preparing tablets, 35 mg of Avicel (microcrystalline cellulose), 15 mg of sodium starch glyconate as the dissolution auxiliary and 80 mg of L-HPC (low-hydroxypropylcellulose) for preparing tablets as the binder. The blend was introduced into a U-type mixer and then mixed for about 20 minutes.

After the mixing is completed, 10 mg of magnesium stearate as the lubricant was further added thereto and then mixed for about 3 minutes. The mixture was subjected to tests for quantitative analysis and moisture content analysis and then compressed into tablets and film-coated to prepare the tablet containing 250 mg of the aqueous mixed extract per one tablet.

Example 4
Preparation of Syrups

A suitable amount of white sugar was dissolved in a given amount of water, and 80 mg of paraoxymethylbenzoate and 16 mg of paraoxypropylbenzoate as the preservatives were added thereto. 4.5 g of the lyophilized powdery mixed extract as obtained in Example 1 was added thereto and completely dissolved with maintaining the temperature at 60° C. The resulting solution was cooled and distilled water was added thereto to make a total volume to 150 ml, thereby producing the desired syrup preparation.

Example 5
Preparation of Capsules 300 mg of the lyophilized powdery mixed extract as obtained in Example 1 was mixed with 200 mg of lactose as the carrier. The mixture was filled in a hard gelatine capsule to produce the desired capsule preparation.

Example 6
Preparation of Beverage Compositions 500 mg of the lyophilized powdery mixed extract as obtained in Example 1 was dissolved in a suitable amount of water and then suitable amounts of vitamin C as the auxiliary component and citric acid, sodium citrate and high fructose as the agent for correcting taste were added thereto. Then, a suitable amount of sodium benzoate as the preservative was added and then water was added thereto to adjust a total volume to 100 ml, thereby producing the desired beverage composition.

Example 7
Preparation of Injection Compositions 200 mg of the lyophilized powdery mixed extract as obtained in Example 1 was heated and dissolved in 200 mg of physiological salt solution containing 1 wt % of polyoxyethylene hydrated castor oil to prepare injection formulation consisting of the mixed extract in a concentration of 0.1 wt %.

Comparative Example 1
Preparation of the Aqueous Extract of *Panax notoginseng*

According to the same procedure as Example 1 except that only *Panax notoginseng* is used as the raw material, the aqueous extract of *Panax notoginseng* was prepared.

Comparative Example 2
Preparation of the Aqueous Extract of *Salvia miltiorrhiza*

According to the same procedure as Example 1 except that only *Salvia miltiorrhiza* is used as the raw material, the aqueous extract of *Salvia miltiorrhiza* was prepared.

Example 8 and Comparative Examples 3 and 4
Comparison of the Hypotensive Effects of the Extracts The hypotensive effects were compared with each other by orally administering each of the single extract of *Panax notoginseng* prepared in Comparative Example 1, the single extract of *Salvia miltiorrhiza* prepared in Comparative Example 2, and the mixed extract prepared in Example 1 once in an amount of 250 mg/kg. In conducting this experiment, rats suffering from genetically induced hypertension (SHR: spontaneous hypertensive rats) were used.

First, in order to use SHR in non-anesthetic state for the experiment the following operation was conducted according to the method proposed by Chiu et al. (Chuang C. Chiueh and Irwin J. Kopin; J. Physiol. 234 (6), H690–H695, 1978).

SHR was anesthetized by intraperitoneally injecting sodium pentobarbital (Entobar prepared by Hanrim Pharm.) in an amount of 50 mg per kg of body weight. Then, polyethylene catheter (PE-50; Clay Adams) filled with heparin solution (500 IU/ml in saline, prepared by Choong-Wai Pharm.) was inserted into left carotid by about 2 cm and pulled out toward the back of neck via subcutaneous layer. In this procedure, the catheter and operating appliances were sterilized with 70% alcohol to use in the operation, the operation site was covered with sulfadiazine powder, and heparin solution was injected into the catheter in an amount of 0.5 ml twice a day in order to prevent the blood coagulation in the catheter. Blood pressure and heart rate were observed 24 hours after insertion of the catheter.

Systolic and diastolic blood pressures were recorded on Grass polygraph (Model 7E, Grass Instrument) by connecting the catheter inserted into carotid directly to Statham pressure transducer (P23 ID) and the mean arterial tension was simultaneously recorded through a separate channel. The pressure transducer was positioned so as to be parallel with the position of rat heart. The heart rate was measured by means of cardio-tachograph (7P44C) of arterial pulse wave through a separate channel.

Rats as transported to measure blood pressure and heart rate were allowed to stand for 2 hours for stabilization and sedation and then, blood pressure and heart rate were measured. Then, each of the single extract of *Panax notoginseng* prepared in Comparative Example 1, the single extract of *Salvia miltiorrhiza* prepared in Comparative Example 2, and the mixed extract prepared in Example 1 was orally administered. The blood pressure and heart rate obtained as the result of experiment were presented on the average of 10 values read for 5 minutes at intervals of 30 seconds, and the systolic blood pressure was separately presented in FIG. 1. SHR not receiving the extract was used as the control group.

As can be seen in FIG. 1, it could be identified that the mixed extract of Example 1 exhibits a significant hypotensive effect in comparison to the control group. Contrary to this, administration of the extract of *Panax notoginseng* prepared in Comparative Example 1 shows a tendency to lower the systolic blood pressure but does not provide a significant difference over the control group. The extract of *Salvia miltiorrhiza* exhibits no hypotensive effect. This result is also identically observed in case of the diastolic blood pressure and the mean blood pressure.

Example 9
Hypotensive Effect Depending on the Amount of the Mixed Extract as Orally Administered Once to Hypertensive Rats In order to observe a change in hypotensive effect depending on the amount of the mixed extract, the mixed extract of Example 1 was orally administered once in an amount of 62.5 mg/kg, 125 mg/kg or 250 mg/kg to hypertensive rats and the test for hypotensive effect was conducted in the same manner as Example 8.

Figure 2:
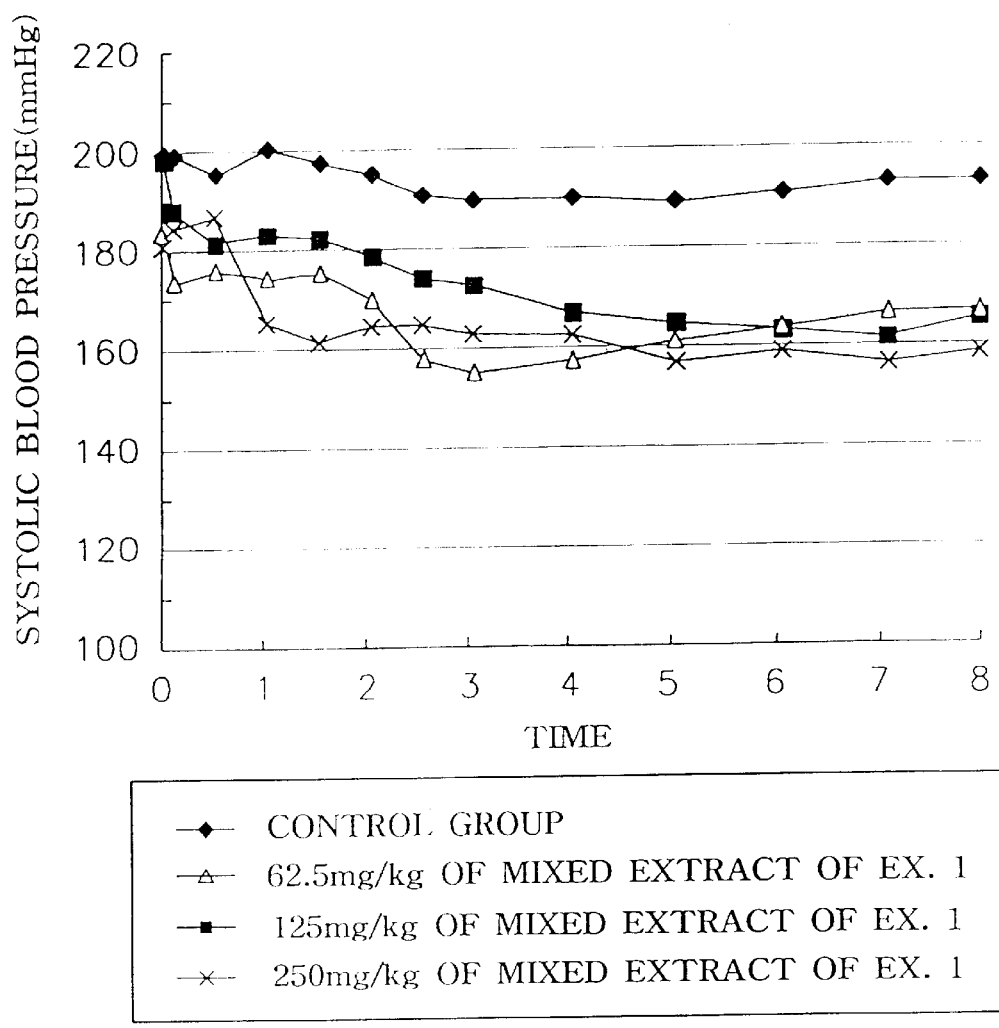
FIG. 2 is a graph showing the effect of lowering systolic blood pressure following a single oral administration of the mixed extract of *Panax notoginseng* and *Salvia miltiorrhiza*, as a result of Example 9.
Figure 3:
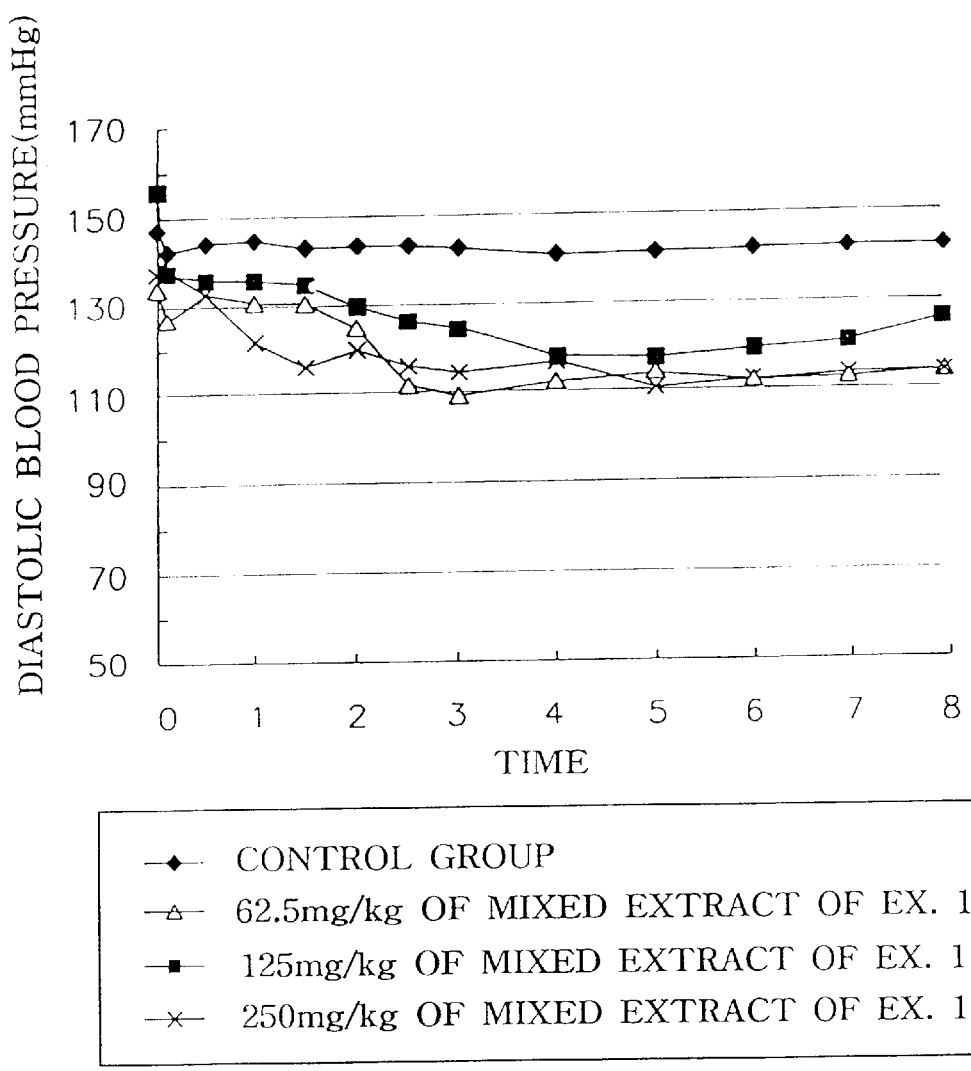
FIG. 3 is a graph showing the effects of lowering diastolic blood pressure following a single oral administration of the mixed extract of *Panax notoginseng* and *Salvia miltiorrhiza*, as a result of Example 9.
Figure 4:
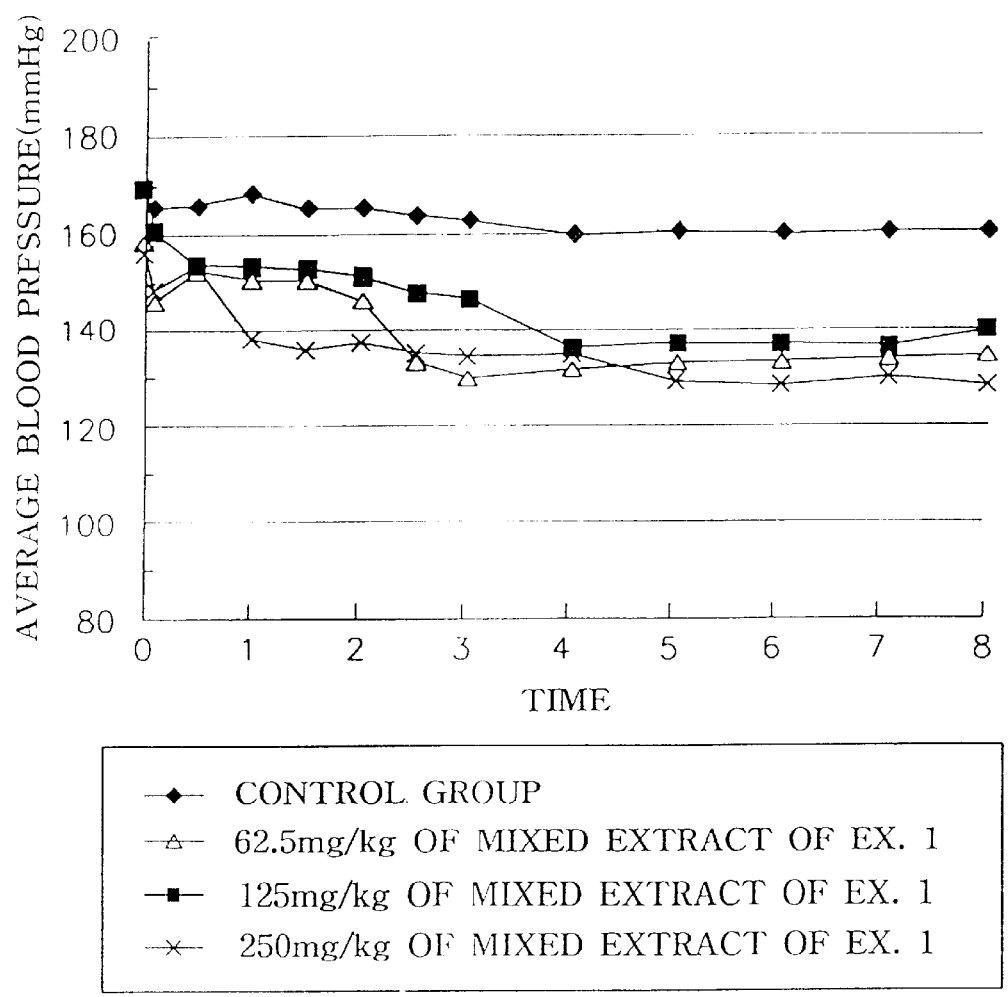
FIG. 4 is a graph showing the effect of lowering mean blood pressure following a single oral administration of the mixed extract of *Panax notoginseng* and *Salvia miltiorrhiza*, as a result of Example 9.

The result of experiment following the oral administration of the mixed extract is presented as the systolic blood pressure in FIG. 2, the diastolic blood pressure in FIG. 3 and the mean blood pressure in FIG. 4. As a result, it could be identified that the hypotensive effect by 15 to 25% is generally obtained in comparison to the control group.

Even at low amount of 62.5 mg/kg a statistically significant hypotensive effect could be observed, but any change in effect dependent on the amount could not be observed. The heart rate was never affected by the extract.

Example 10
Hypotensive Effect Following Multiple Oral Administration of the Mixed Extract to Hypertensive Rats The following experiment was conducted in order to observe any change in blood pressure when the mixed extract of the present invention is administered in many times.

SHR in which hypertension is genetically induced is the most ideal animal model for human essential hypertension and accompanies cerebral stroke in at least 70% thereof and spontaneously induces cerebral thrombosis, and therefore, was used in this experiment.

Three-weeks aged 35 SHRs (male) were selected. Among them, the control group comprising 15 rats received saline and two test group each of which comprises 10 rats received 125 mg/kg and 250 mg/kg, respectively, of the mixed extract of Example 1 via oral route. The administration was continued for 6 weeks once a day, during which blood pressure was measured at the same time once a week and then compared with blood pressure before administration of the test drug.

Figure 5:
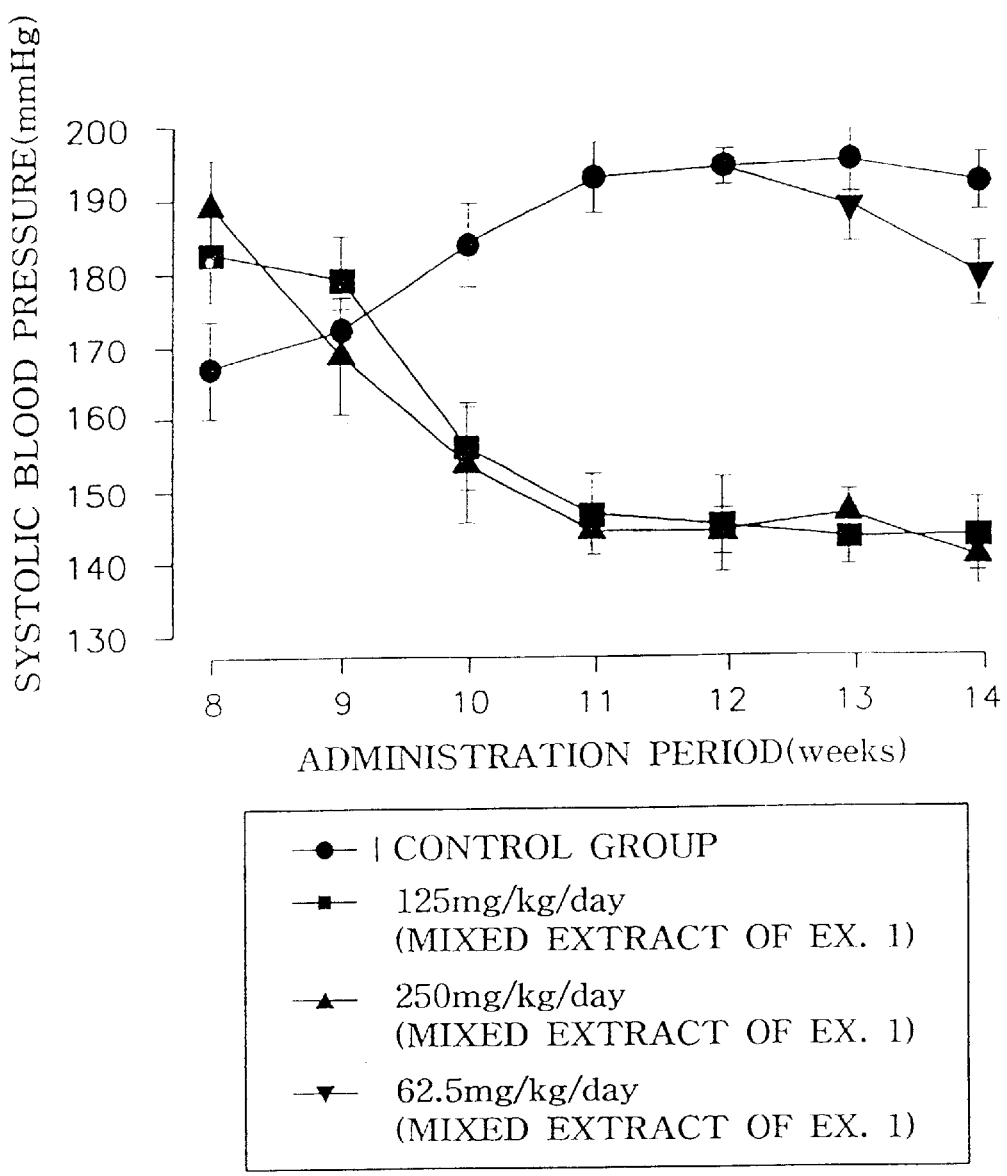
FIG. 5 is a graph showing the effect of lowering systolic blood pressure following multiple oral administration of the mixed extract of *Panax notoginseng* and *Salvia miltiorrhiza*, as a result of Example 10.
Figure 6:
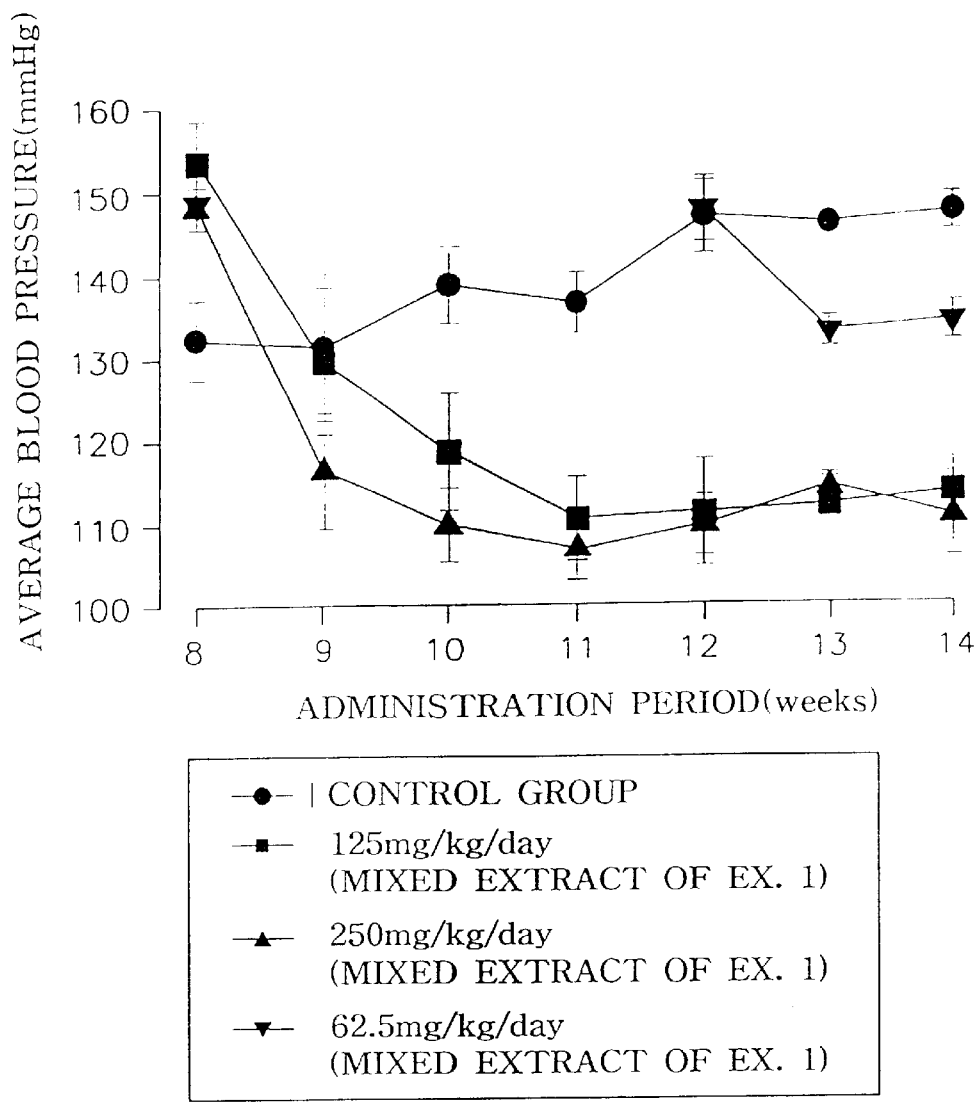
FIG. 6 is a graph showing the effects of lowering mean blood pressure following multiple oral administration of the mixed extract of *Panax notoginseng* and *Salvia miltiorrhiza*, as a result of Example 11.
Figure 7:
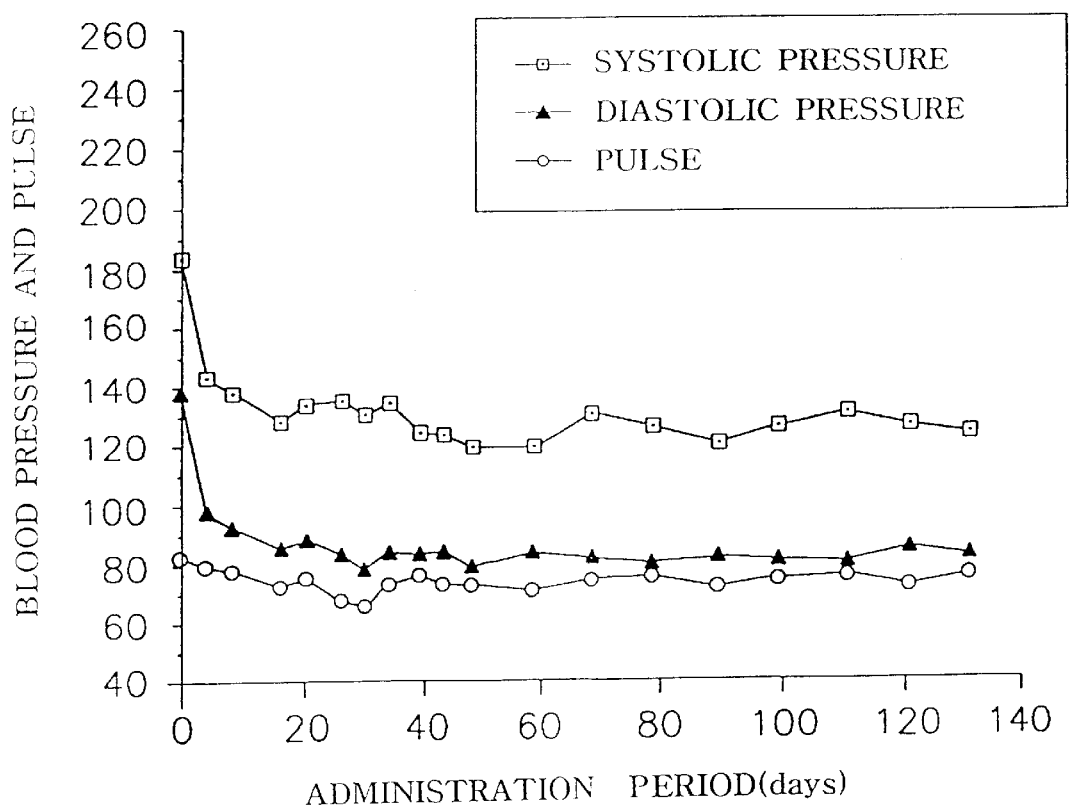
FIG. 7 is a graph showing the change of blood pressure in the clinical case receiving the mixed extract of *Panax notoginseng* and *Salvia miltiorrhiza*, as a result of Example 12.
Figure 8:
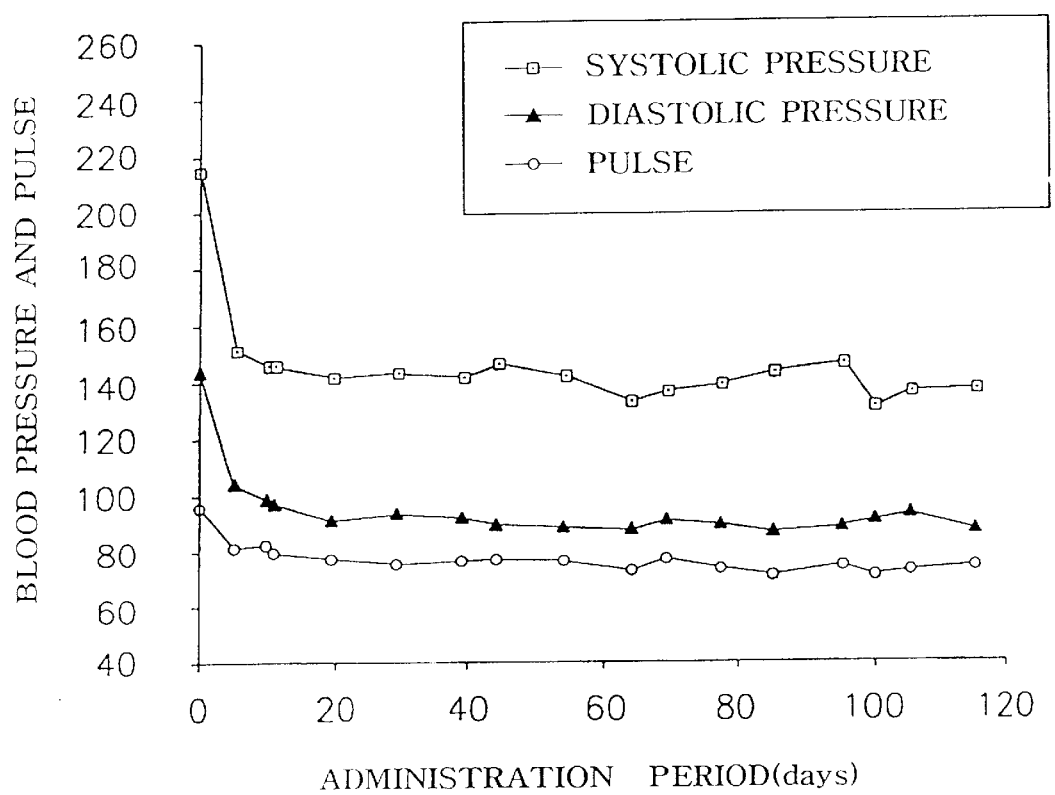
FIG. 8 is a graph showing the change of blood pressure in the clinical case receiving the mixed extract of *Panax notoginseng* and *Salvia miltiorrhiza*, as a result of Example 12.
Figure 9:
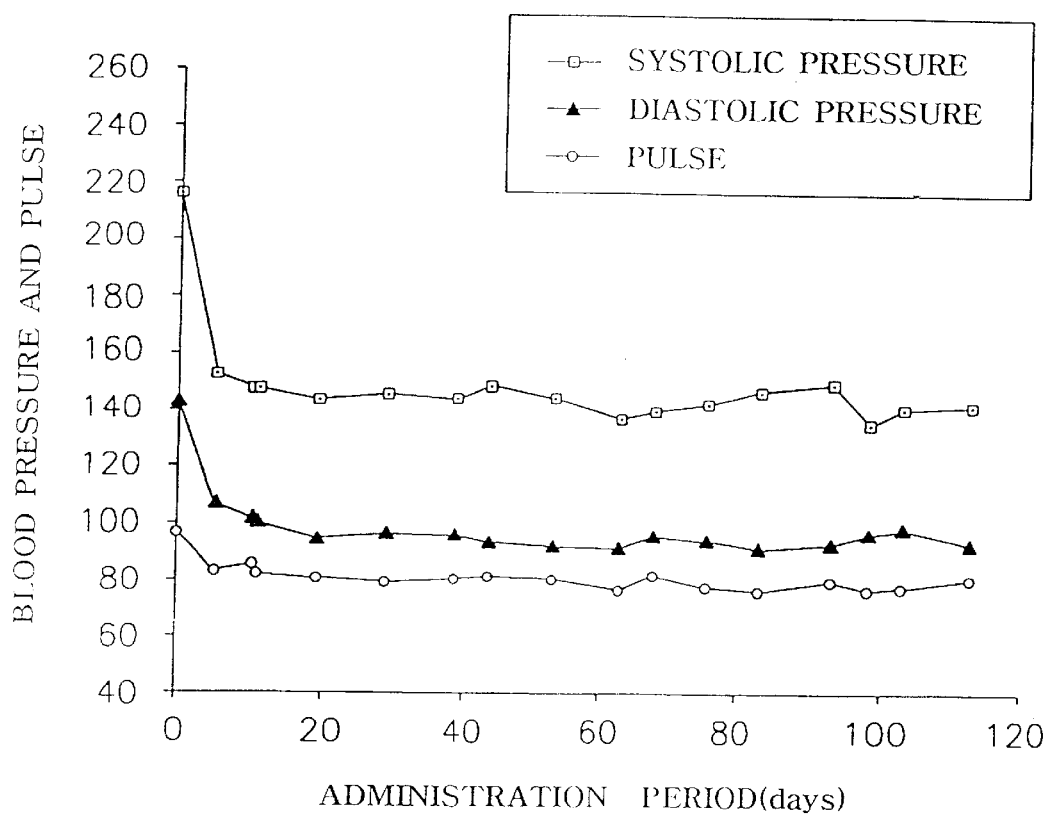
FIG. 9 is a graph showing the change of blood pressure in the clinical case receiving the mixed extract of *Panax notoginseng* and *Salvia miltiorrhiza*, as a result of Example 12.
Figure 10:
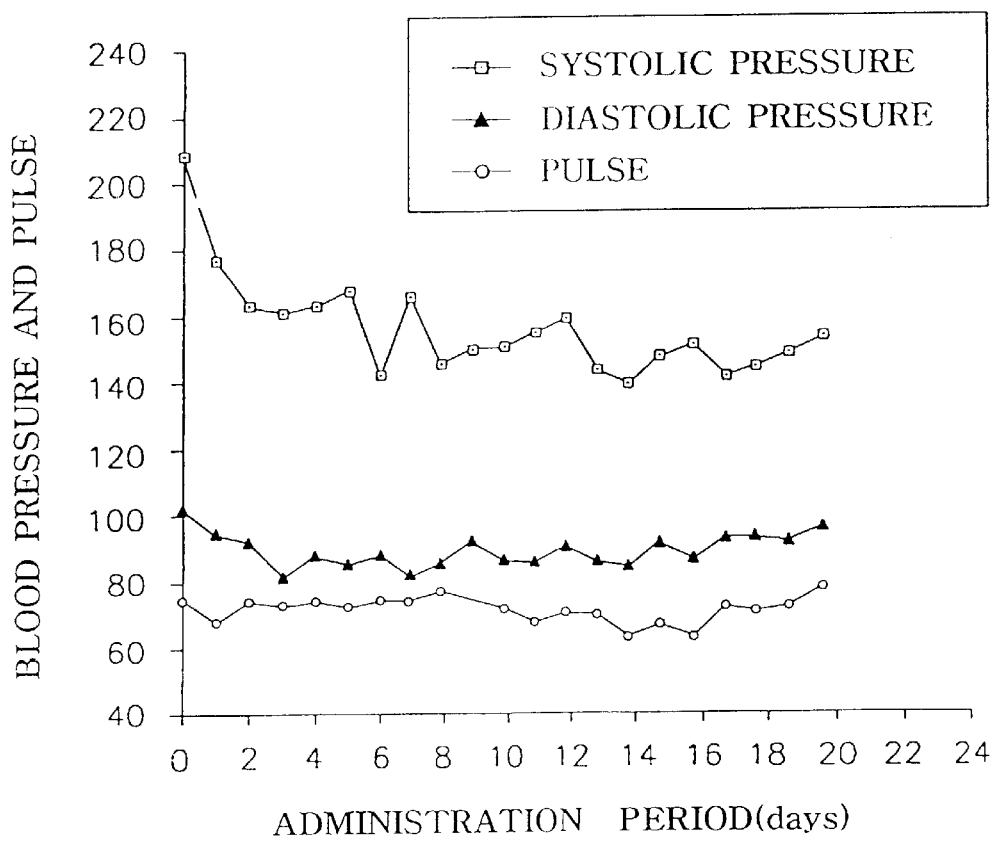
FIG. 10 is a graph showing the change of blood pressure in the clinical case receiving the mixed extract of *Panax notoginseng* and *Salvia miltiorrhiza*, as a result of Example 12.

FIG. 5 shows the systolic blood pressure by administration period and FIG. 7 shows the mean arterial pressure by administration period. It could be found that all the control group shows the continuous increase in blood pressure without any exception whereas both the test groups receiving the mixed extract show the gradual decrease in blood pressure to reach within the normal range.

In addition, 5 of 15 rats in the control group, all of which show an increase in blood pressure, were randomly selected and were given the mixed extract of Example 1 in an amount of 62.5 mg/kg via oral route. As a result, the increased blood pressure was reversed and lowered. The hear rate measured together with blood pressure has never changed.

Example 11
Test for Acute Toxicity in ICR Mouse

To identify the safety of the mixed extract of *Panax notoginseng* and *Salvia miltiorrhiza* according to the present invention $LD_{50}$ value (amount which can kill 50% of the experimental animals) of the drug as the standard index for acute toxicity was determined according to the following method.

36 normal ICR mice (male, 22±1 g) were divided into 6 groups A thorough F wherein each group contains 6 mice. Group A was used as the control group receiving physiological saline and the mixed extract of *Panax notoginseng* and *Salvia miltiorrhiza* prepared in Example 1 according to the present invention was orally administered to Group B in an amount of 1 g and, with gradually increasing the amount, to Group C in an amount of 2.5 g, to Group D in an amount of 5 g, to Group E in an amount of 7.5 g and to Group F in an amount of 10 g. Then, $LD_{50}$ value of the mixed aqueous extract administered per orally (p.o.) was determined by Behrens-Kärber method (see Japan, p131, 1960). The result is described in the following Table 1.

TABLE 1

Lethal dose ($LD_{50}$) of the mixed aqueous extract of *Panax notoginseng* and *Salvia miltiorrhiza* administered via oral route

| Test Group | Dosage (g/kg) | Oral administration (p.o.) No. of died animals/No. of used animals | Z | d |
|---|---|---|---|---|
| A | 0 | 0/6 | — | — |
| B | 1 | 0/6 | 0 | 1.0 |
| C | 2.5 | 0/6 | 0 | 1.5 |
| D | 5 | 0/6 | 0 | 2.5 |
| E | 7.5 | 0/6 | 0 | 2.5 |
| F | 10 | 0/6 | 0 | 2.5 |

In the above table, z is the half value (½) of the number of died animals at two consecutive dosages and d represents a difference between two consecutive dosages.

As can be seen from the result described in the above Table 1, no animal died even in the group to which the mixed aqueous extract of *Panax notoginseng* and *Salvia miltiorrhiza* according to the present invention was administered in a high dosage of 10 g per 1 kg of body weight. In other words, it can be apparently noted that the mixed aqueous extract of *Panax notoginseng* and *Salvia miltiorrhiza* according to the present invention can be safely administered with substantially no toxicity.

The autopsy and pathologic histological assay for the experimental animals used for measurement of $LD_{50}$ value were conducted according to the following manner.

After completion of the experiment, all the viable animals were anesthetized with ether and sacrificed by bleeding. Then, the desired organs were extracted and any abnormality of the organs was macroscopically examined. To conduct the pathological histological assay, all the dissected organs were fixed in 10% neutral formalin solution for 10 days or more, and then dried, embedded with a paraffin embedder (Fisher, Histomatic Tissue Processor, 166A), cut off in 5 µm section by means of AO Rotary Microtome and then stained with hematoxylin and eosin. Then, the condition of stained organs was observed.

The pathological histological protocol of the dissected organs of all the experimental animals in each group examined by microscope is as follows. Specifically, any abnormality in tissues due to the administration of the mixed aqueous extract of *Panax notoginseng* and *Salvia miltiorrhiza* according to the present invention was not found even in mouse to which the mixed aqueous extract is administered via oral route in an amount of 10 g per kg of body weight. In addition, kidney did not show any abnormality due to drug administration and myocardial cells in heart did also not show any abnormality. Other major organs including gastro-intestinal tract, pancreas, lung, spleen, adrenal gland, brain, testis, ovary, bone marrow, etc. did not show any abnormalities.

Therefore, it could be determined that the mixed aqueous extract of *Panax notoginseng* and *Salvia miltiorrhiza* according to the present invention has no side effect due to acute toxicity in all organs even by administration of 10 g per kg of body weight as the maximum dosage which can be administered to mouse, and further, is a safe drug which does not induce toxicity including any damage of organs.

Example 12

Clinical Cases

Four hypertensive patients were given the mixed extract of the present invention in a dosage of 1.5 g per day to observe the change of blood pressure. The results of measuring systolic blood pressure, diastolic blood pressure and pulse at the same time every day before and after administration are represented in FIGS. 7 to 10, respectively.

The effect of controlling blood pressure following the smooth lowering of blood pressure was observed immediately after administration. The hypotensive effect was observed in all patients but does not induce the lowering of blood pressure under the optimum level. Therefore, it is determined that the mixed extract of the present invention is effective for controlling blood pressure.

Example 13 and Comparative Examples 5 and 6

Comparison of Properties of the Extracts by UV Absorbance

Figure 11:
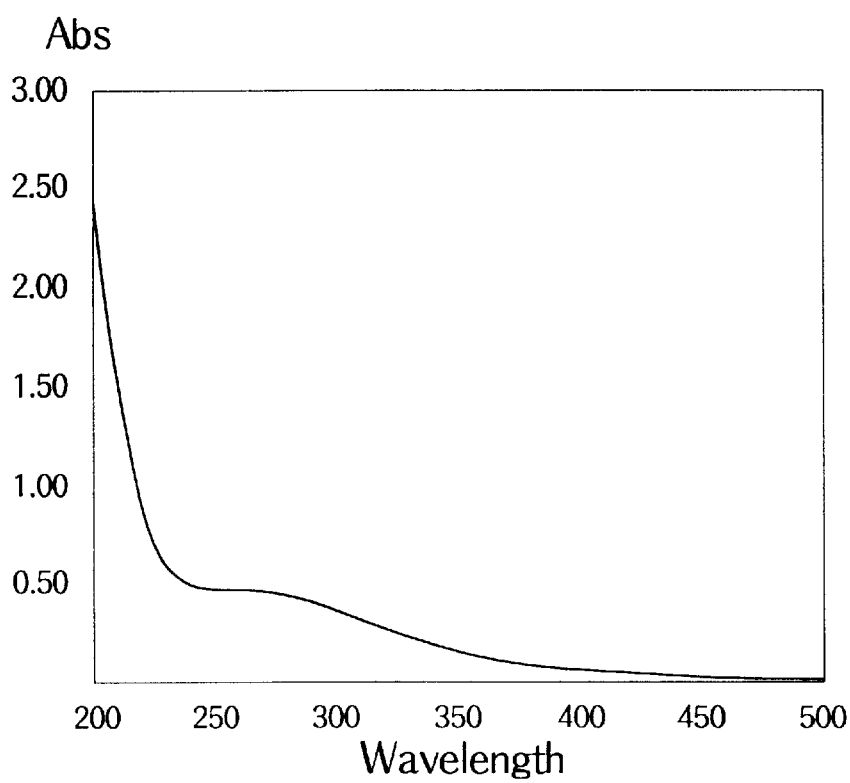
FIG. 11 is a UV spectrogram of the extract of *Panax notoginseng*, as a result of Comparative Example 5.
Figure 12:
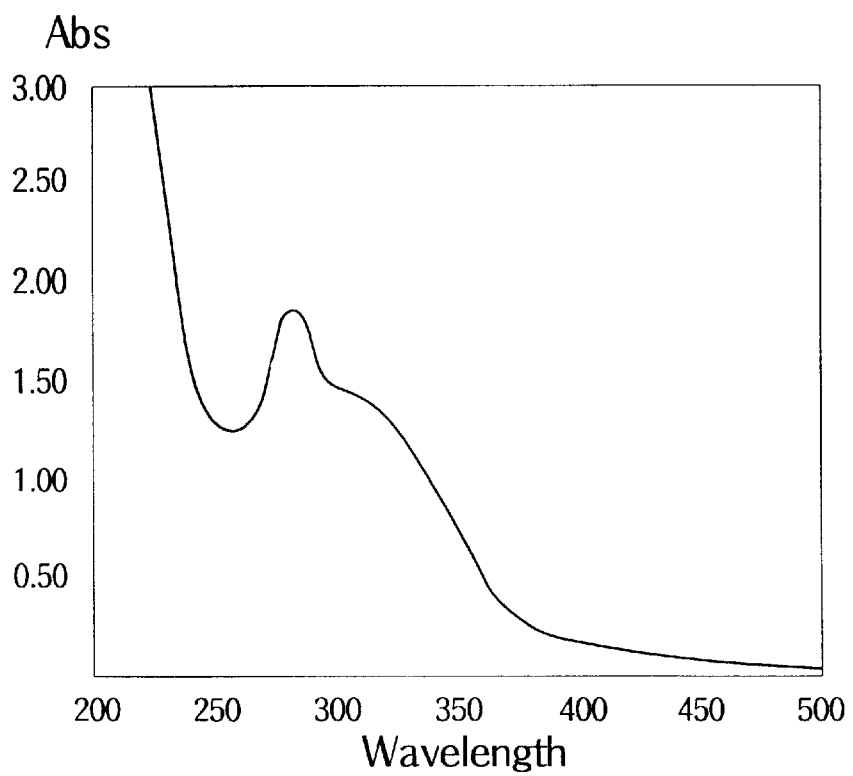
FIG. 12 is a UV spectrogram of the extract of *Salvia miltiorrhiza*, as a result of Comparative Example 6.
Figure 13:
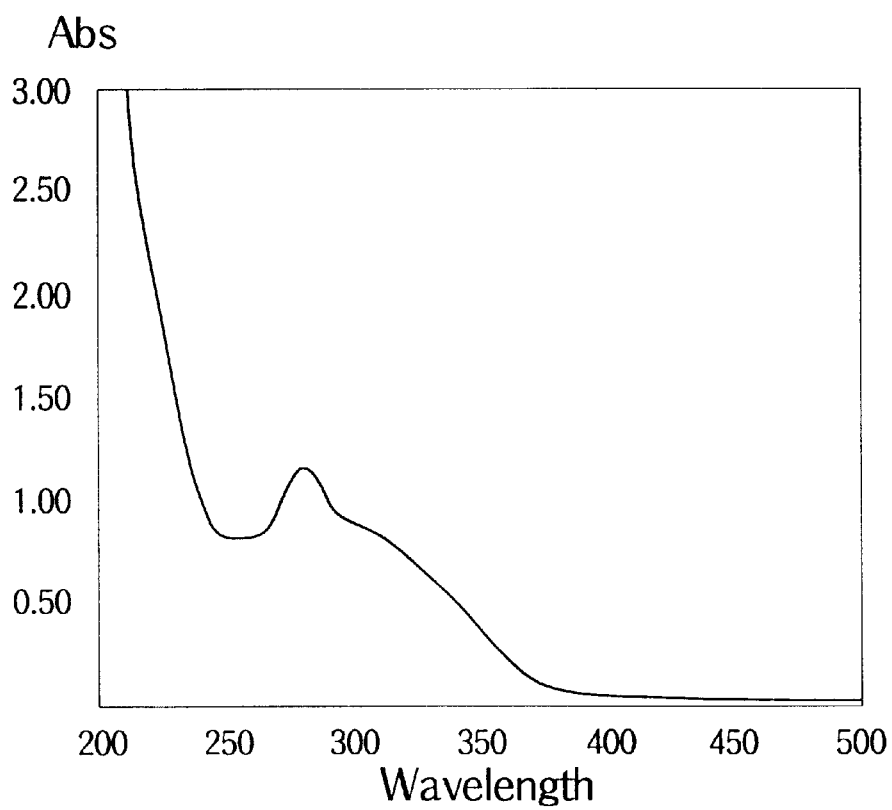
FIG. 13 is a UV spectrogram of the mixed extract of *Panax notoginseng* and *Salvia miltiorrhiza*, as a result of Example 13.

The single extract of *Panax notoginseng* prepared in Comparative Example 1, the single extract of *Salvia miltiorrhiza* prepared in Comparative Example 2, and the mixed extract of *Panax notoginseng* and *Salvia miltiorrhiza* as prepared in Example 1 were analyzed by means of UV spectrophotometer (Ultrospec 2000) to show the results in FIGS. 11, 12 and 13, respectively.

FIG. 11 shows the result of measuring UV absorbance of the single extract of *Panax notoginseng*. It shows the phenomenon that the single extract of *Panax notoginseng* has a very low absorbance and therefore, does substantially not absorb the light between 200–500. Since many of saponins do not absorb ultraviolet lay, it is considered that *Panax notoginseng* has a high content of saponins.

FIG. 12 shows the result of measuring UV absorbance of the extract of *Salvia miltiorrhiza*, which shows an increase in absorbance at 283 nm.

FIG. 13 is a UW spectrogram of the mixed extract of *Panax notoginseng* and *Salvia miltiorrhiza* according to the present invention and shows an increase of absorbance at 283 nm as in case of the extract of *Salvia miltiorrhiza*.

Example 14 and Comparative Examples 7 and 8

Comparison of Properties of the Extracts by HPLC (High Performance Liquid Chromatography)

Figure 14:
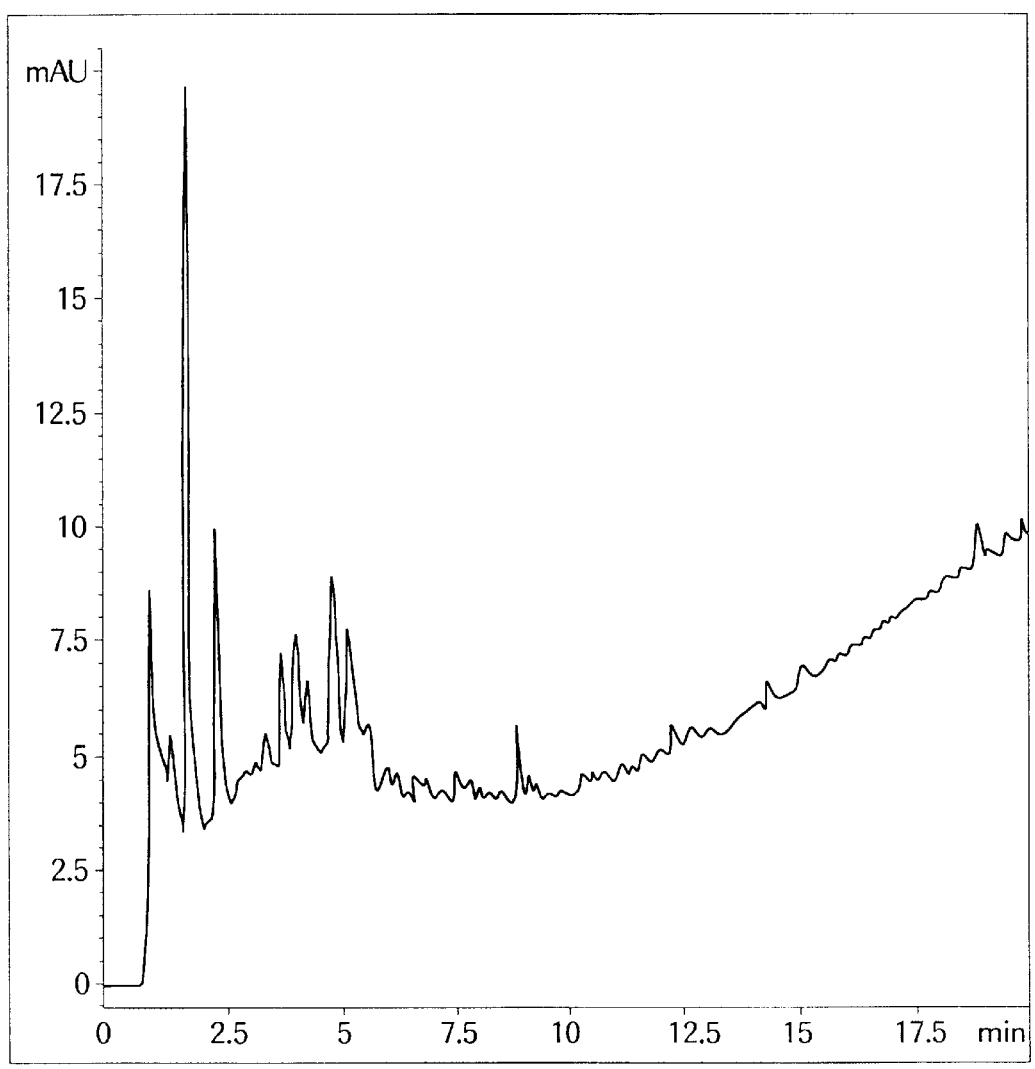
FIG. 14 is a HPLC chromatogram of the extract of *Panax notoginseng*, as a result of Comparative Example 7.
Figure 15:
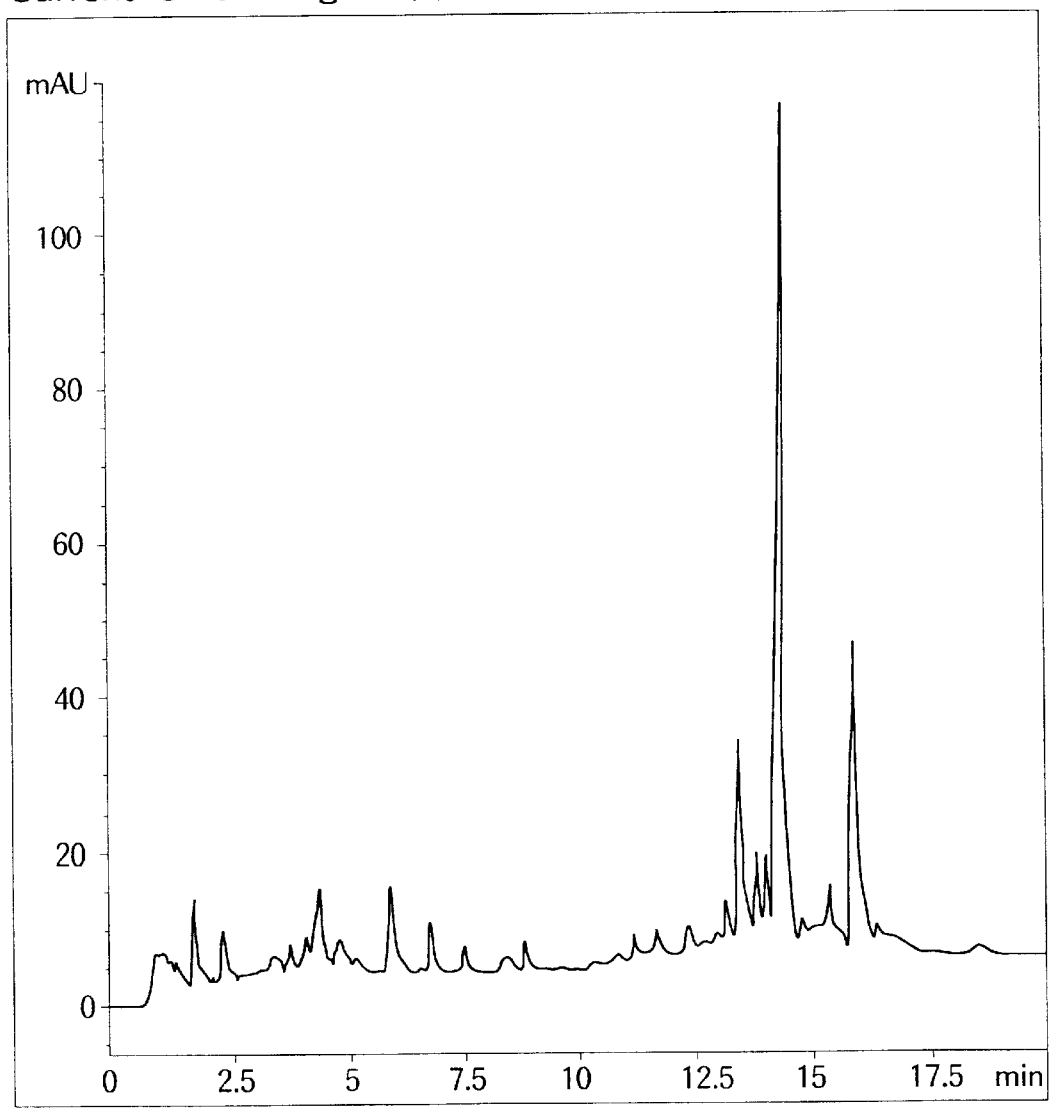
FIG. 15 is a HPLC chromatogram of the extract of *Salvia miltiorrhiza*, as a result of Comparative Example 8.
Figure 16:
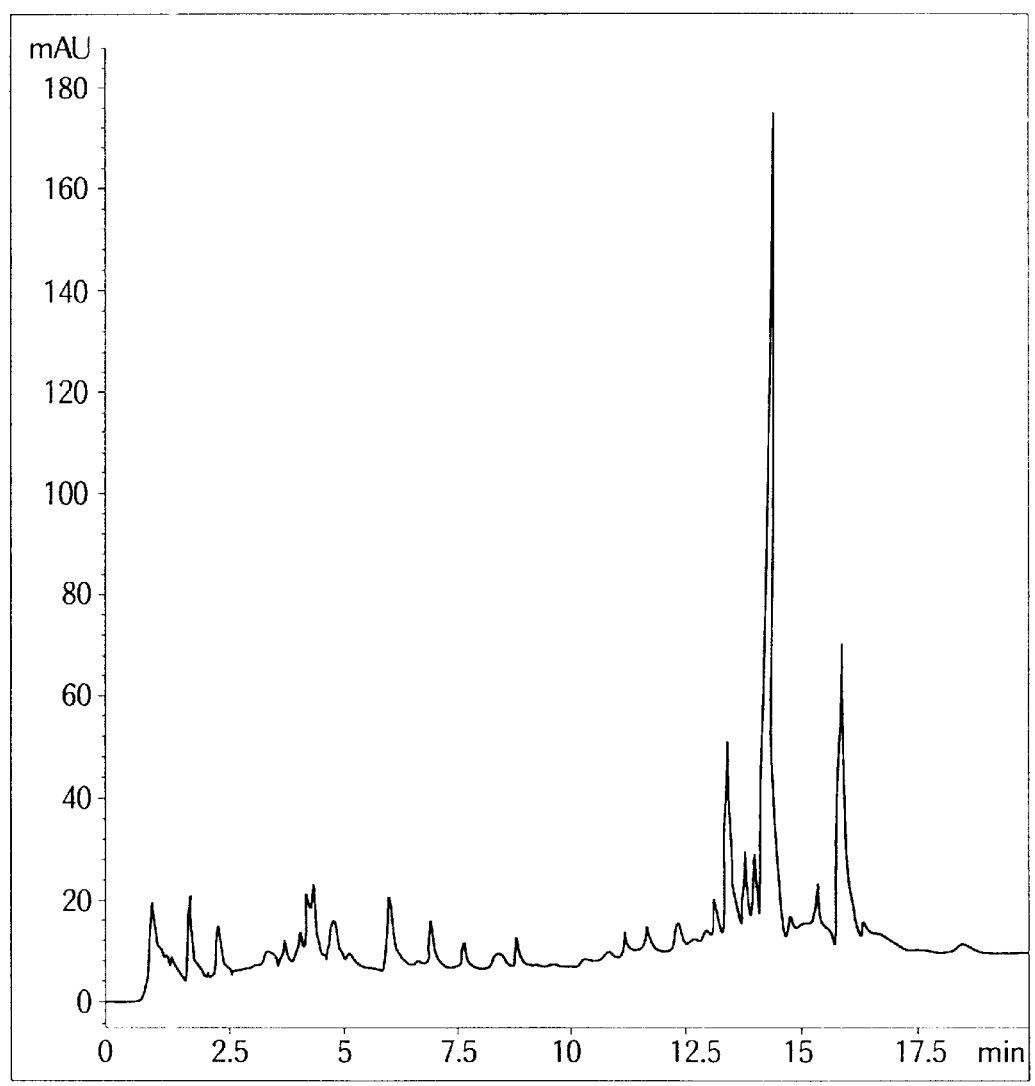
FIG. 16 is a HPLC chromatogram of the mixed extract of *Panax notoginseng* and *Salvia miltiorrhiza*, as a result of Example 14.

The single extract of *Panax notoginseng* prepared in Comparative Example 1, the single extract of *Salvia miltiorrhiza* prepared in Comparative Example 2, and the mixed extract of *Panax notoginseng* and *Salvia miltiorrhiza* as prepared in Example 1 were analyzed by means of HPLC (Model HP1090) to show the results in FIGS. 14, 15 and 16, respectively.

For HPLC, the pre-treatment of the extracts were carried out by dissolving each of the single aqueous extracts in the concentration of 1 mg/ml and the mixed aqueous extract in the concentration of 2 mg/ml, in water. 10 µl of the dissolved extract solution was taken and applied to HPLC for analysis.

The conditions for analysis are as follows:

Column: C18 ODS; 4.6 mm i.d.×100 mm L

Mobile phase: gradient system of 1% acetic acid and methanol varying from 100:0 to 0:100 over 30 minutes Flow rate: 1 ml/min.

Detection: measured at 254 nm by means of photodioid array detector

In HPLC chromatograms, the characteristic peaks were observed for each specimen and also identically reproduced even in repeat experiments. The results are as follows.

FIG. 14 is a HPLC chromatogram of the extract of *Panax notoginseng*, in which characteristic peaks are observed at 0.985 min., 1.789 min., 4.861 min. and 8.781 min.

FIG. 15 is a HPLC chromatogram of the extract of *Salvia miltiorrhiza*, in which characteristic peaks are observed at 6.030 min., 13.270 min., 14.115 min. and 15.716 min.

FIG. 16 is a HPLC chromatogram of the mixed extract of *Panax notoginseng* and *Salvia miltiorrhiza*, in which it appears that a peak at 2.392 min. is derived from *Panax notoginseng* and characteristic peaks at 1.3390 min., 14.215 min and 15.813 min are derived from *Salvia miltiorrhiza*.

Example 15

Influence upon Plasma Cholesterol

Sprague-Dawley rats were divided into two group in which one was given a synthetic diet comprising 1% cholesterol and 10% corn oil and the other was given orally the same diet together with the aqueous extract of *Panax notoginseng* prepared in Comparative Example 1, the aqueous extract of *Salvia miltiorrhiza* prepared in Comparative Example 2, and the mixed aqueous extract prepared in Example 1. Plasma cholesterol levels in two groups were compared with each other.

The result is shown in the following Table 2. As can be seen from Table 2, when the extract of *Panax notoginseng* or *Salvia miltiorrhiza* is administered in an amount of 30 mg/kg, a statistically significant effect of decreasing cholesterol level was not observed whereas the mixed extract of the present invention induces a decrease of total cholesterol level by 28.2%, a decrease of LDL-cholesterol level by 35.5% (p<0.05) and an increase of HDL-cholesterol by 23.8%. Further, since the mixed extract of the present invention provides a significant effect in a ratio between HDL-cholesterol and total cholesterol and a ratio between HDL-cholesterol and LDL-cholesterol, it is strongly suggested that the mixed extract of the present invention has an activity for lowering the possibility of occurring arteriosclerosis.

TABLE 2

Influence of the extract of *Panax notoginseng*, the extract of *Salvia miltiorrhiza* and the mixed extract on plasma cholesterol level in rats fed with high cholesterol

| Class | Control group | Aqueous extract of PN[1) ] (30 mg/kg) | Aqueous extract of SM[2) ] (30 mg/kg) | Mixed aqueous extract (30 mg/kg) |
|---|---|---|---|---|
| Total cholesterol (mg/dl) | 245 ± 54 | 230 ± 36 | 201 ± 30 | 176 ± 31 (28.2%) |
| HDL-cholesterol (mg/dl) | 23.1 ± 5.0 | 22.4 ± 1.9 | 23.8 ± 1.9 | 28.6 ± 1.5 (23.8%) |
| LDL-cholesterol (mg/dl) | 203 ± 59 | 189 ± 33 | 161 ± 24 | 131 ± 31* (35.5%) |
| HDL-C/T-C ratio | 0.10 ± 0.04 | 0.10 ± 0.02 | 0.12 ± 0.02 | 0.17 ± 0.03* |
| HDL-C/LDL-C ratio | 0.13 ± 0.06 | 0.12 ± 0.03 | 0.15 ± 0.04 | 0.23 ± 0.05* |

In the above table, 1) PN means *Panax notoginseng*, 2) SM means *Salvia miltiorrhiza*, * denotes the comparative value of two groups under the condition of P<0.05 in t-test for verifying the significance with the control group, HDL-C/T-C ratio means the ratio of HDL-cholesterol/total cholesterol, and HDL-C/LDL-C ratio means the ratio of HDL-cholesterol/LDL-cholesterol.

The present invention relates to a composition extracted from two kinds of medicinal herbal plants, *Panax notoginseng* and *Salvia miltiorrhiza*, which exhibits an effect of smoothly controlling-improving blood pressure to the normal level without causing side effects in cardiac, renal and cerebrovascular systems as generally occurred due to the prior agents for treatment of hypertension, when the composition of the present invention is administered in order to improve human hypertension to the normal blood pressure. Further, the composition of the present invention is also characterized in that it does not lower the blood pressure under the normal level, and does not induce any subjective and objective abnormality.

In other word, the composition of the present invention is the natural substance for controlling blood pressure which can be used as the therapeutic agent for hypertension for a long period without side effects in clinical field, and at the same time, the natural substance for preventing arteriosclerosis and cardiac and vascular disorders by lowering the plasma cholesterol level.

While the invention has been described with respect to the above specific embodiments, it should be recognized that various modifications and changes can be made to the invention by those skilled in the art which also fall within the scope of the invention as defined by the appended claims.

What is claimed is:

1. A composition for treating hypertension and lowering cholesterol level, which comprises a mixed extract of *Panax notoginseng* and *Salvia miltiorrhiza* as an active ingredient, wherein *Panax notoginseng* and *Salvia miltiorrhiza* are mixed in a mixing ratio of 5:1–1:5 by weight of the total composition.

2. The composition for treating hypertension and lowering cholesterol level as defined in claim 1, which further comprises a pharmaceutically acceptable excipient.

3. The composition for treating hypertension and lowering cholesterol level as defined in claim 2, which is formulated into any one selected from the group consisting of tablet, capsule, solution suspension and syrup.

4. The composition for treating hypertension and lowering cholesterol level as defined in claim 1, wherein the extract is an aqueous extract.

5. The composition for treating hypertension and lowering cholesterol level as defined in claim 1, wherein the extract is an alcoholic extract.

6. The composition for treating hypertension and lowering cholesterol level as defined in claim 1, wherein the mixing ratio of *Panax notoginseng* and *Salvia miltiorrhiza* is 2:1–1:2 by weight of the total composition.

* * * * *